US006322579B1

(12) United States Patent  (10) Patent No.: US 6,322,579 B1
Müller  (45) Date of Patent: Nov. 27, 2001

(54) SLIDING SHAFT SURGICAL INSTRUMENT

(76) Inventor: Robert Müller, Max-Planck-Strasse 5/2 C, 78549 Spaichingen (DE)

( * ) Notice: Subject to any disclaimer, the term of this patent is extended or adjusted under 35 U.S.C. 154(b) by 0 days.

(21) Appl. No.: 09/532,846

(22) Filed: Mar. 21, 2000

(51) Int. Cl.$^7$ .................................................. A61B 17/00
(52) U.S. Cl. ........................ 606/205; 606/170; 606/174; 600/564
(58) Field of Search ........................ 606/1, 108, 174, 606/170, 171, 180, 205, 51, 52; 600/564

(56) References Cited

U.S. PATENT DOCUMENTS

| 2,113,246 | 4/1938 | Wappler ................. 128/321 |
| 2,790,437 | * 4/1957 | Moore .................... 606/170 |
| 4,662,371 | * 5/1987 | Whipple et al. ........... 606/174 |
| 5,133,727 | 7/1992 | Bales et al. . |
| 5,159,374 | 10/1992 | Groshong . |
| 5,273,519 | 12/1993 | Koros et al. . |
| 5,282,800 | 2/1994 | Foshee et al. . |

FOREIGN PATENT DOCUMENTS

| 78 01 891 U1 | 7/1978 | (DE) . |
| 90 07 356.8 | 6/1991 | (DE) . |
| 41 15 937 A1 | 5/1992 | (DE) . |
| 693 12 754 T2 | 8/1993 | (DE) . |
| 94 21 125.6 | 6/1995 | (DE) . |
| 44 24 659 A1 | 1/1996 | (DE) . |
| 196 28 589 A1 | 1/1998 | (DE) . |

* cited by examiner

*Primary Examiner*—David O. Reip
*Assistant Examiner*—William Lewis
(74) *Attorney, Agent, or Firm*—Pendorf & Cutliff

(57) ABSTRACT

A surgical sliding shaft instrument (10) comprising a guide element (12), which is provided with a carriage (14). It further includes a grip part element (16), which is comprised of a stationary grip part (18), one end of which is provided with a grip trunk (20) pivotably linked to the guide element (12) and also releasably inter-locked with the guide element (12). It further includes a movable grip part (22), which is pivotally connected to the grip trunk (20) and, via a push part (24) extending through a slit in the grip trunk (20), is in operable engagement with the carriage (14). A compression spring (28) tensions or biases the movable grip part (22) in a rest position. An inter-locking element (26) serves for releasable connecting of the grip trunk (20) and guide element (12). The compression spring (28) is integrated in the carriage (14) and pretensions both the carriage (14) as well as the movable grip part (22) in a rest position.

8 Claims, 2 Drawing Sheets

SLIDING SHAFT SURGICAL INSTRUMENT

BACKGROUND OF THE INVENTION

1. Field of the Invention

The invention concerns a sliding shaft surgical instrument.

2. Description of the Related Art

A sliding shaft instrument of this type is known from U.S. Pat. No. 5,273,519 or corresponding DE 41 15 937 A1. This surgical sliding shaft instrument includes a guide element adapted for receiving a carriage. The sliding shaft instrument further includes a grip element, which is comprised of a stationary grip part, of which one end is provided with an arm pivotably connected with the guide element and releasably connectable to the guide element. Further, a moveable grip part is provided, which is pivotably linked to the arm, and which is in engagement with the carriage via a push part extending through a slit or through-hole in the arm, for operation thereof. Further, a compression spring is provided between the two grip parts, in order to pretension the moveable grip part in a rest position. Via a locking mechanism, the connection between the arm and the guide element can be released. The sliding shaft instrument further exhibits a rotation means for adjustment of the angular position of the work carriage.

In order to operate the carriage via the push part, the proximal end of the carriage is provided with a rod-shaped projection, on the end of which a ball-shaped projection is provided. In order to be able to move the carriage upon movement of the moveable grip part, this ball-shaped projection must be seated in a corresponding receptacle of the push part.

To do this it is however necessary to be able to observe a seating process from the outside. For this reason, the guide element is provided with a through-hole or window. This construction is not only expensive since various construction components must be precisely dimensioned with respect to each other, it also causes the seating process of the individual parts to be difficult and time-consuming.

U.S. 2,113,246 discloses a surgical instrument in which a compression spring is integrated in a carriage, which pretensions a moveable grip part in a starting position. For change-out of the carriage, this is seated upon a saddle, wherein a circular longitudinal section must be positioned with a thereto connecting shoulder and an oppositely lying segment positioned on a rib-shaped projection of the shoulder. Subsequently, a closing part is pivoted over the work carriage and locked with the shoulder. At the same time, the moveable grip part, the upper end of which forms a take-along fork, is introduced in a ring-notch or recess of the moveable part of the carriage, wherein the moveable part must be displaced or slid against the action of the compression spring and temporarily held in a particular position in order to make possible the seating upon the fork of the moveable grip part.

It is considered to be disadvantageous, that the seating of the work carriage is comparatively difficult and inconvenient to accomplish. There is also the danger, that during the attempt of seating the moveable part upon the fork under pretension of the spring, that this escapes upwardly and jumps out of the shoulder, before the locking part pivots back and can be locked closed. =p Further, the instrument is so conceived, that for operation of the moveable mouth part, the two grip parts must be pulled apart. These have grip-eyes at their lower ends, without which the operation of the instrument would not be possible. The movement direction is ergonomically inconvenient and makes difficult a targeted and precise force transmission. For the application of greater forces, it is in certain cases even necessary to use both hands to pull the grip parts apart at the grip eyes.

SUMMARY OF THE INVENTION

The invention is based on the task, of providing a surgical sliding shaft instrument of the above-described type, wherein a simplified construction of the instrument is made possible by a technical simplification.

The essential concept of the invention is comprised therein, that the compression spring necessary for the operation of the sliding shaft instrument is integrated in the carriage. This compression spring always tensions the carriage in its starting or—as the case may be—rest position. On the basis of the provision of the compression spring in the carriage, it is no longer necessary to mechanically connect or couple the carriage with the push part of the moveable grip part. The engagement between the carriage and the push part of the moveable grip part is accomplished essentially by a touching contact of the push part against the proximal end of the carriage. Therewith, via the touch contact between the proximal end of the carriage and the push part, the moveable grip part is also simultaneously pretensioned in its starting or—as the case may be—rest position.

The compression spring is herein provided lying against a register or stop collar at the proximal end of the carriage, wherein this stop collar is in touch contact with the push part.

The closure element includes a spring-loaded pretensioned catch-hook, which can be brought into engagement with a locking hook provided correspondingly at the proximal end of the guide element.

Therein, the catch-hook is preferably pretensioned by means of a leaf spring and operable via an outward facing pressure plate provided on the stationary grip part and operable for the locking engagement of the connection between the guide element and the grip trunk.

This type of locking is substantially more secure in comparison to the locking means used in the above-described state of the art since here, as a result of the design, an unintentional release of the engagement of between the guide element and the grip trunk is no longer possible.

The locking element according to the above-described state of the art, in comparison, is comprised essentially of a small locking device provided in the area of the grip trunk, which can be easily released by unintentional contact.

The sliding shaft instrument can advantageously include a re-orientation or rotation means, with which the angular position of the carriage can be adjusted.

Preferably the rotation means is a perforated ring or wheel connected to the carriage fixed against rotation, and in engagement with a pin, which is moveable via a release lever provided outside on the grip trunk.

In contrast to the above-described known state of the art, the rotation means includes no star wheel which, to be re-oriented, requires an operating person to extract an engagement tooth with two fingers of a free hand towards the proximal end of the sliding shaft instrument. Since the operating person must hold the sliding shaft instrument with the other hand, it becomes possible to adjust the angle of rotation only with the aid of an additional person.

With the help of the release lever provided outside on the grip trunk, which is supported upon a pivot or stud in a rocker-like manner, the operating person can operate the release lever with one finger, usually the index finger, of the respective hand with which the operating person is holding the two grip parts of the sliding shaft instrument.

Thereby the angular adjustment is not only significantly simplified, it is also made more reliable.

The stationary grip part can include an outwardly projecting horn or bulge, against which the hand of the operating person can be supported for better handling or manipulation.

In order to make possible a complete disassembly of the sliding shaft instrument for cleaning purposes, the grip trunk can be connected with the guide element via a removable pin.

The same applies for the moveable grip part, which can be linked via a removable pivot pin in the area of the grip trunk.

As the material for the sliding shaft instrument, surgical steel is preferred.

BRIEF DESCRIPTION OF THE DRAWINGS

In the following, the invention will be described in greater detail on the basis of the illustrative embodiment shown in the drawings. There is shown.

DETAILED DESCRIPTION OF THE INVENTION

Figure 1:
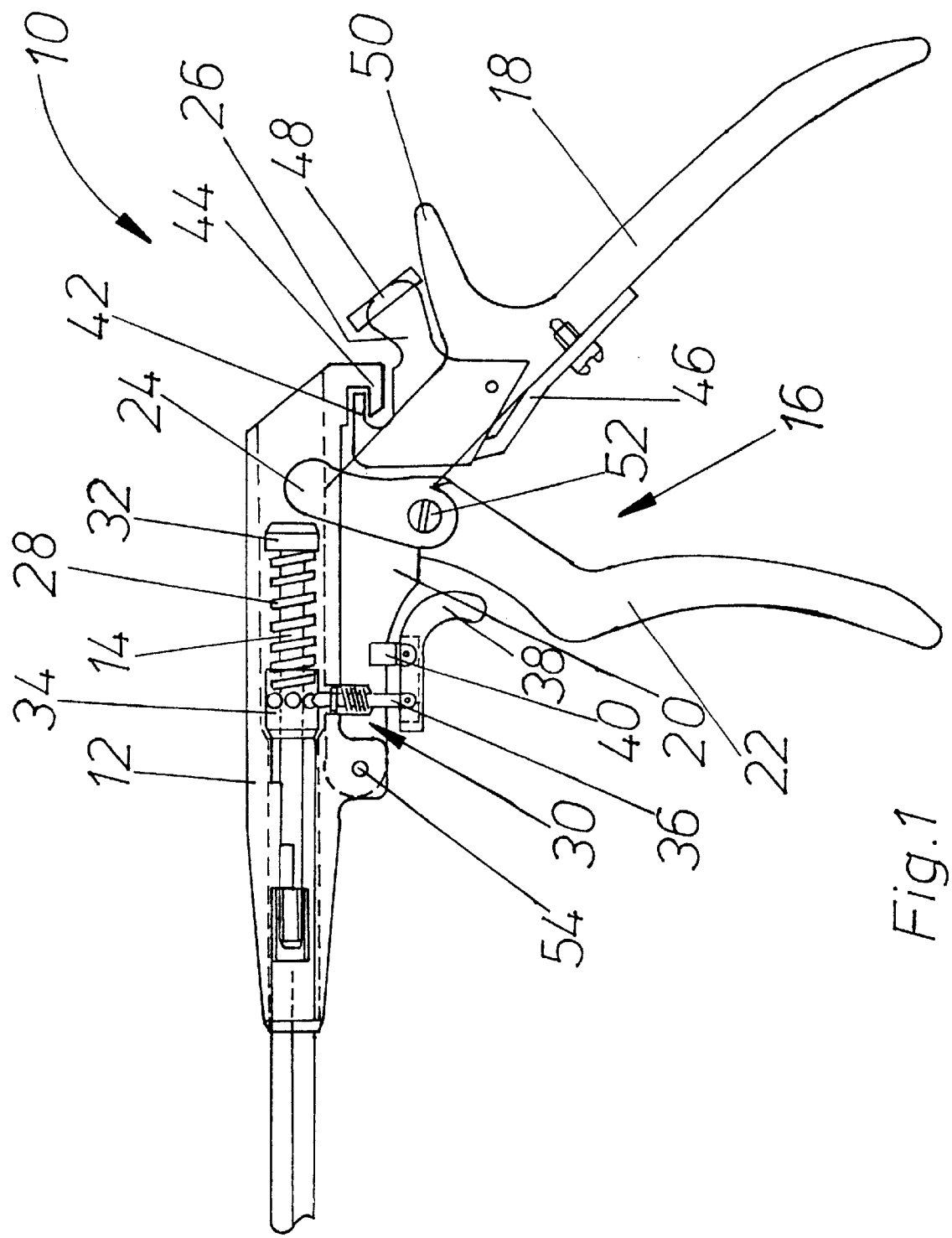
FIG. 1 a partial axial sectional side view of a sliding shaft instrument in operable condition.

A sliding shaft instrument 10 is comprised of a guide element 12, which can receive a carriage 14.

A grip part element 16 is connected to the guide element 12. The grip part element 16 is comprised of a stationary grip part 18 with one grip trunk 20 provided on one end, which is pivotally connected to the guide element 12 via a releasable pivot pin 52.

In order to interlock the stationary grip part 18 with the guide element 12, a locking element 26 is provided at the transition of the stationary grip part 18 to the grip trunk 20.

The grip trunk 20 includes a slit or through-hole, not shown in the drawings, through which the moveable grip part 22 extends with a push part 24 provided on one end of the moveable grip part 22.

The moveable grip part 22, in the area of its transition to the push part 24, is secured to the grip trunk 20 via a removable pivot pin 52.

Figure 2:
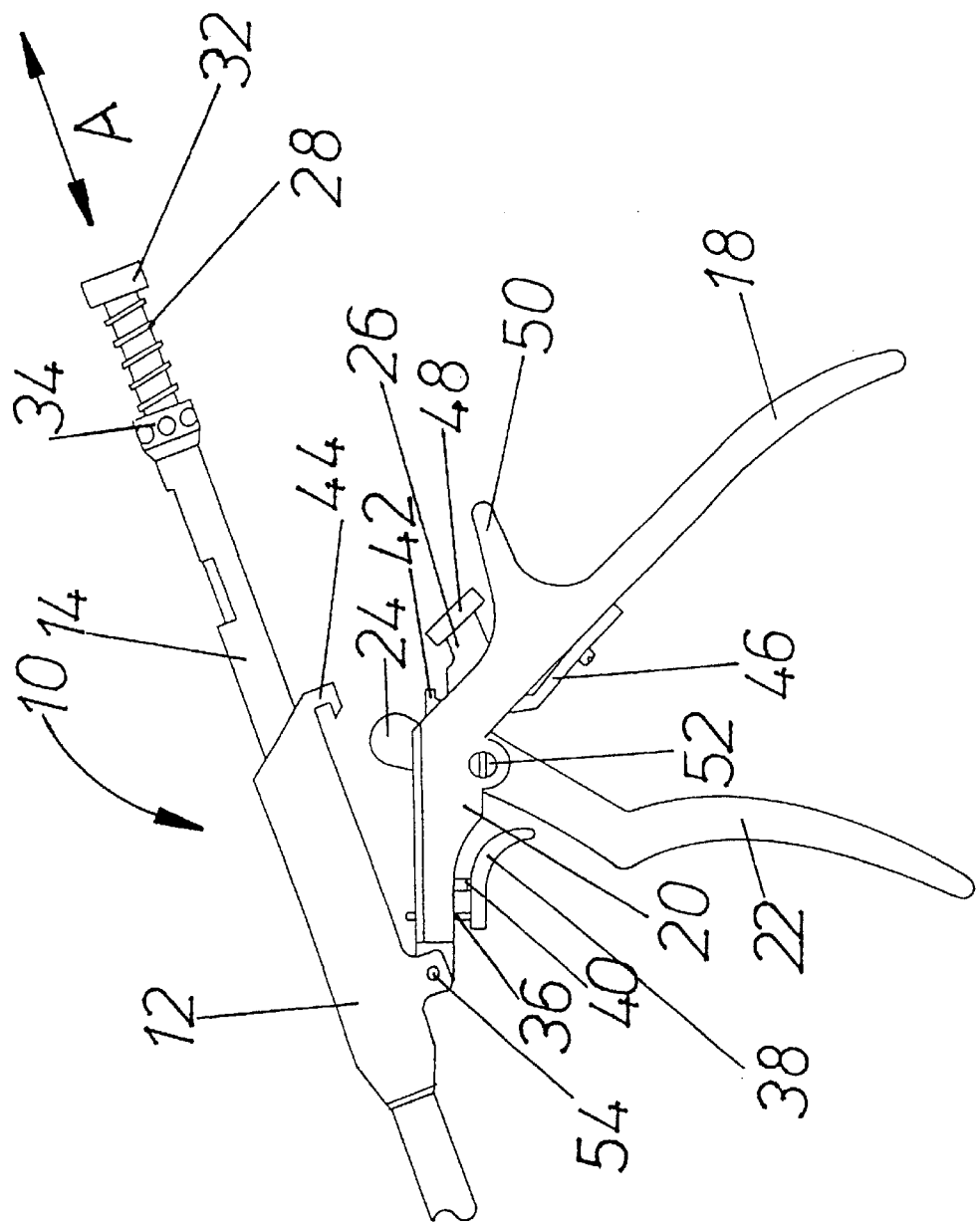
FIG. 2 a partial side view of the sliding shaft instrument in open condition for changing out of a carriage.

As can be clearly seen from FIGS. 1 and 2, the carriage 14 has at its proximal end a compression spring 28, which is provided between an adjustment device 30 for the angular position of the carriage 14 and a register or stop collar 32. The side of the stop collar 32 opposite to the spring is in contact with the push part 24.

Thereby, the compression spring 28 causes not only the carriage 14, but also the moveable grip part 22 to be pretensioned in a start or—as the case may be—resting position.

As can be seen from FIG. 1, the adjustment device 30 for the rotational positioning of the carriage 14 is comprised of a wheel or ring with holes 34, the ring fixed against rotation on the carriage 14, and in engagement with a pin 36 which can be operated via a release lever 38 provided outside on the grip trunk 20. The release lever 38 is provided with a curvature in the direction of the moveable grip part 22, so that this release lever 38 can in simple manner be operated with one finger, usually the index finger, of the operating person.

Between the curvature of the release lever 38 and the pin 36, the release lever 38 is connected in the manner of a rocker to a stud or post 40 which is in turn connected to the grip trunk 20 As a result, a simple operation of the release lever 38 in the area of the curvature leads to a vertical movement of the pin 36, which is pretensioned in the engagement position via a not shown spring, such that the pin can be moved vertically downwards.

This simple construction of the adjustment device 30 makes possible the holding of the sliding shaft instrument 10 as well as the operation of the rotational adjustment device 30 with one hand of an operating person, while the other hand can rotate the carriage 14 in simple manner to the desired position.

A further special feature with respect to the state of the art concerns the inter-locking element 26. This inter-locking element 26 includes a spring-loaded catch hook 42, which can be brought into engagement with a locking hook 44 correspondingly provided on the proximal end of the guide element 12. Thereby, the catch hook 42 is so designed that its hook area is directed outwards, while the locking hook 44 is correspondingly directed inwards.

This inter-locking element 26 can be pretensioned by means of a leaf spring 46, which is secured to the moveable grip part 22 facing side of the stationary grip part 18 for example via a not in greater detail shown screw, and can be unlocked via a pressure plate 48 provided on the stationary grip part 18 and facing outwardly, for example by the operating person pressing with the thumb.

In order to provide the hand of the operating person with a secure grip, the stationary grip part 18 is provided with a horn 50 below and bordering on the locking element 26 and projecting outwards, against which the hand of the operating person can be placed.

The surgical sliding shaft instrument 10 can be brought into the opened position shown in FIG. 2 by pressing the pressure plate 48. By the appropriate pressing of the pressure plate 48 against the tension force of the leaf spring 46 the catch hook 42 of the locking element 26 is displaced in the direction of the moveable grip trunk 20 and released from the locking hook 44 of the guide element 12

Consequently, the guide element 12 can be pivoted about the pivot pin 54. In this position, the carriage 14 can be extracted in simple manner and a new carriage 14, or as the case may be, another carriage 14, can be introduced in simple manner. The corresponding movement directions of the carriage 14 are schematically shown by a double arrow A.

The new carriage 14 needs to be slid into the guide element 12 until the rotation adjustment device 30 for the angular position of the carriage 14 abuts against a, not in greater detail shown, end stop in the guide element 12.

By a simple pivoting of the guide element 12 and the grip part element 16 towards each other until an engagement of the catch hook 42 with the locking hook 44 the sliding shaft instrument 10 is already operable, since as a result of this pivot movement the push part 24 of the moveable grip part 22 is brought into touching contact with the proximal end facing surface of the stop collar 32. Thereby, the sliding shaft instrument 10 is brought into operational condition in only a few seconds.

Also, the disassembly of the sliding shaft instrument 10 can be carried out in a manner of a few seconds for a cleaning and sterilization.

For this, it is essentially only necessary, as already described above, that the inter-locking element 26 is disengaged, the carriage 14 extracted, the grip part element 16 removed by releasing, or as the case may be, extraction of the pivot pin 54 and the moveable grip part 22 removed by extraction by the pivot pin 52. Thereby, all individual components can be conveniently cleaned and sterilized.

The assembly occurs in the reverse manner of the above-described disassembly.

REFERENCE NUMBER LIST

10 Sliding shaft instrument
12 Guide element
14 Carriage
16 Grip part element
18 Stationary grip part
20 Grip trunk
22 Moveable grip part
24 Push part
26 Locking element
28 Compression spring
30 Adjustment device
32 Abutment or end stop
34 Wheel with holes
36 Pin
38 Release lever
40 Stud
42 Engagement hook
44 Locking hook
46 Leaf spring
48 Pressure plate
50 Horn
52 Rotation pin
54 Pivot pin

What is claimed is:

1. Surgical sliding shaft instrument including:
a guide element,
a carriage in sliding engagement with said guide element,
a grip element comprising a grip trunk, a stationary grip part, wherein one end of the stationary grip part is pivotably linked a to the guide element and wherein the stationary grip part is releasably interlocked with the guide element, and a movable grip part, wherein the movable grip part is pivotably linked to the grip trunk and wherein the moveable grip part is in operable engagement with the carriage via a push part which extends through a through-hole in the grip trunk,
a compression spring for pretensioning of the moveable grip part in a starting or rest position, and
a locking element for releasably connecting of the grip trunk and guide element,
wherein the compression spring (28) is integrated in the carriage (14) and pretensions both the carriage (14) as well as the movable grip part (22) in the starting or rest position,
wherein the compression spring (28) lies against a register (32) provided at the proximal end of the carriage (14) and wherein the register (32) is in touching contact with the push part (24), and
wherein the inter-locking element (26) includes a spring-tensioned catch hook (42), which is in engagement with a locking hook (24) provided at the proximal end of the guide element (12).

2. Sliding shaft instrument according to claim 1, wherein the catch hook (42) is pre-tensioned via a leaf spring (46), and wherein the connection between the guide element (12) and the grip trunk (20) can be disengaged by operating a pressure plate (48) provided on the stationary grip part (18) and facing outwards.

3. Surgical sliding shaft instrument including:
a guide element,
a carriage in sliding engagement with said guide element,
a grip element comprising a grip trunk, a stationary grip part, wherein one end of the stationary grip part is pivotably linked to the guide element and wherein the stationary grip part is releasably interlocked with the guide element, and a movable grip part, wherein the movable grip part is pivotably linked to the grip trunk and wherein the moveable grip part is in operable engagement with the carriage via a push part which extends through a through-hole in the grip trunk,
a compression spring for pretensioning of the moveable grip part in a starting or rest position, and
a locking element for releasably connecting of the grip trunk and guide element,
wherein the compression spring (28) is integrated in the carriage (14) and pretensions both the carriage (14) as well as the movable grip part (22) in the starting or rest position,
wherein the compression spring (28) lies against a register (32) provided at the proximal end of the carriage (14) and wherein the register (32) is in touching contact with the push part (24),
wherein the inter-locking element (26) includes a spring-tensioned catch hook (42), which is in engagement with a locking hook (24) provided at the proximal end of the guide element (12; and wherein the instrument further includes
a rotational adjustment device (30) for adjusting the angular orientation of the carriage (14).

4. Sliding shaft instrument according to claim 3, wherein the adjustment device (30) includes a wheel or ring with holes (34) provided fixed against rotation on the carriage (14), in which a pin (36) engages, which pin is operable by means of a release lever (38) provided outside on the grip trunk (20), which release lever (38) is supported upon a pivot support (14).

5. Sliding shaft instrument according to claim 1, wherein the stationary grip part (18) includes an outwardly directed horn (50).

6. Surgical sliding shaft instrument including:
a guide element,
a carriage in sliding engagement with said guide element,
a grip element comprising a grip trunk, a stationary grip part, wherein one end of the stationary grip part is pivotably linked to the guide element and wherein the stationary grip part is releasably interlocked with the guide element, and a movable grip part, wherein the movable grip part is pivotably linked to the grip trunk and wherein the moveable grip part is in operable engagement with the carriage via a push part which extends through a through-hole in the grip trunk,
a compression spring for pretensioning of the moveable grip part in a starting or rest position, and
a locking element for releasably connecting of the grip trunk and guide element,
wherein the compression spring (28) is integrated in the carriage (14) and pretensions both the carriage (14) as well as the movable grip part (22) in the starting or rest position,
wherein the compression spring (28) lies against a register (32) provided at the proximal end of the carriage (14) and wherein the register (32) is in touching contact with the push part (24),
wherein the inter-locking element (26) includes a spring-tensioned catch hook (42), which is in engagement with a locking hook (24) provided at the proximal end of the guide element (12), and wherein the grip trunk (20) is connected with the guide element (12) via a releasable pivot pin (54).

7. Sliding shaft instrument according to claim 1, wherein the movable grip part (22) in the area of transition to the push part (24) is pivotably connected to the grip trunk (20) via a releasable pivot pin (52).

8. Sliding shaft instrument according to claim 1, wherein said instrument is comprised of surgical steel.

* * * * *